United States Patent [19]

Ardeshir et al.

[11] Patent Number: 4,978,621
[45] Date of Patent: Dec. 18, 1990

[54] MEROZOITE SURFACE ANTIGENS

[75] Inventors: Feroza Ardeshir, San Diego; Janette E. Flint, Del Mar; Robert T. Reese, La Jolla, all of Calif.

[73] Assignee: Scripps Clinic and Research Foundation, La Jolla, Calif.

[21] Appl. No.: 366,191

[22] Filed: Jun. 1, 1989

Related U.S. Application Data

[63] Continuation of Ser. No. 775,758, Sep. 3, 1985, abandoned.

[51] Int. Cl.$^5$ .................... C12N 1/00; C12N 1/500; C12N 1/22; C12P 21/06
[52] U.S. Cl. ................... 435/243; 435/69.8; 435/172.3; 435/252.33; 536/27; 935/18; 935/29; 935/48; 935/56; 935/65; 935/73; 935/81
[58] Field of Search ............ 435/68, 172.1, 172.3, 435/252.33, 320, 243, 69.1, 69.8, 71.2, 91; 935/18, 27, 41, 47, 56, 65, 73; 536/27

[56] References Cited

FOREIGN PATENT DOCUMENTS 2154592 9/1985 United Kingdom .

OTHER PUBLICATIONS

Perrin et al. (1984), J. Exp. Med. 160:441-451.
Mc Garvey et al. (1984), PNAS 81:3690-94.
Odink et al. (1984) Molecular and Biochemical Parisitology 10: 55-66.
Kemp et al. (1983) PNAS 80: 3787-91.
Reese et al. (1981) Am. J. Trop. Med. 30:1168-78.
Langsley et al. Nucl. Acids Res. vol. 13, pp. 4191-4202 (1985).
Kemp et al. Proc. Nat'l. Acad. Sci. U.S.A., vol. 80, pp. 3787-3791, (1983).
Reese et al. Am. J. Trop. Med Hys. vol. 30, pp. 1168-1178, (1981).
R. F. Howard et al., Mol. Biochem. Parasitol, 17(1), (Abstract) 61-78 (1985).
Perrin et al., *Nature* (London) 289, 301-303, (1981).
Howard et al., *Mol. Biochem. Parasitol.* 17, 61-77, (1985).
Lehninger *Biochemistry* 2nd Ed. (1975), p. 72.
Ardeshir et al., *EMBO J.* 6, 493-499, (1987).
Holder et al., *Nature* (London) 317, 270-273, (1985).
Cheung et al., *EMBO J.* 4, 1007-1012, (1985).
Howard et al., *Gene*, 46:197-205, (1986).
Nicholls et al., *Mol. Biochem. Parasitol.* 28:11-20, (1988).

*Primary Examiner*—Robin L. Teskin
*Assistant Examiner*—Joan Ellis
*Attorney, Agent, or Firm*—Dressler, Goldsmith, Shore, Sutker & Milnamow

[57] ABSTRACT

DNA sequences are described which encode *Plasmodium falciparum* merozoite antigenic surface proteins and protein fragments. Corresponding recombinant plasmids and transformed bacterial strains are described. The proteins and fragments have utility for immunological and diagnostic purposes.

6 Claims, No Drawings

MEROZOITE SURFACE ANTIGENS

This application is a continuation, of application Ser. No. 775,758, filed Sept. 13, 1985 now abandoned.

The invention described herein was supported by the Agency for International Development, Contract No. DPE-0453-C-00-1017-00.

This invention relates to DNA sequences encoding antigenic proteins, or antigenic fragments thereof, which are present on the surface of *Plasmodium falciparum* merozoites. This invention also relates to proteins and fragments so encoded and their use for immunological and diagnostic purposes.

The worldwide resurgence of human malaria, despite attempts to control this disease by vector eradication and drug treatment, makes the development of an antimalaria vaccine a very desirable goal. A protective vaccine against *Plasmodium falciparum*, the species which causes the most severe form of human malaria, will probably have to include antigens from at least two developmental stages of the parasite: the sporozoites, which are injected into the blood by the mosquito, and which appear to contain one immunodominant antigen, Cochrane, A. H., Santoro, F., Nussenzweig, V., Gwadz, R. W. and Nussenzweig, R. S. (1982) *Proc. Natl Acad. Sci. U.S.A.* 79, 5651–5655; and the asexual blood stages, which contain many immunogens, Perrin, L. H. and Dayal R. (1982) *Immunological Rev.* 61, 245–269 (Perrin, et al.); Newbold, C. I. (1984) *Mol. Biochem. Parasitol.* 11, 1–22, only some of which are candidates for protective antigens.

Data from several investigations indicate that most of the putative protective antigens of asexual stage parasites are present in schizonts and merozoites, the more mature developmental forms of the asexual cycle, Perrin et al.; Siddiqui, W. A. (1977) *Science* 197, 388–389; Reese, R. T., Trager, W., Jensen, J. B., Miller, D. A. and Tantravahi, R. (1978) *Proc. Natl. Acad. Sci. U.S.A.* 75, 5665–5668; Brown, G. V., Coppel, R. L., Vrbova, H., Grumont, R. J. and Anders, R. F. (1982) *Exp. Parasitol.* 53, 279–284. However, large-scale production of pure antigens from parasites grown in culture is impractical and expensive because of the requirement for human blood products. One approach towards, identifying, characterizing, and perhaps, producing specific plasmodial antigens is the cloning and expression of parasite genes in bacteria. An important development was the cloning and characterization of the gene for a major sporozoite surface antigen, Dame, J. B., Williams, J. L., McCutchan, T. F., Weber, J. L., Wirtz, R. A., Hockmeyer, W. T., Maloy, W. L., Haynes, J. D., Schneider I., Roberts, D., Sanders, G. S., Reddy, E. P., Diggs, C. L. and Miller, L. H. (1984) *Science* 225, 593–599; Enea, V., Ellis, J., Zavala, F., Arnot, D. E., Asavanich, A., Masuda, A. Quakyi, I. and Nussenzweig, R. S. (1984) *Science* 225, 628–629. Two groups have reported the construction of expression libraries containing genes which are transcribed during the asexual blood cycle of *P. falciparum*, Kemp, D. J., Coppel, R. L., Cowman, A. F., Saint, R. B., Brown, G. V. and Anders, R. F. (1983) *Proc. Natl. Acad. Sci. U.S.A.* 80, 3787–3791 (Kemp et al.); McGarvey, M. J., Sheybani, E., Loche, M. P., Perrin, L. and Mach, B. (1984) *Proc. Natl. Acad. Sci. U.S.A.* 81, 3690–3694 (McGarvey et al.). A major problem for all investigators has been the identification of those clones corresponding to protective antigens. Kemp et al. made a cDNA library in the expression vector lambda gtll-Amp 3, and screened the library with immune human sera. There have been reports of analysis of two antigens expressed by clones from this library: the heat-stable S-antigen, which varies greatly among parasite isolates, Coppel, R. L., Cowman, A. F., Lingelbach, K. R., Brown, G. V., Saint, R. B., Kemp, D. J. and Anders, R. F. (1983) *Nature* (London) 306, 751–756; and a 155k protein which is believed to be located on the surface of parasitized erythrocytes, Coppel, R. L., Cowman, A. F., Anders, R. F., Bianco, A. E., Saint, R. B., Lingelbach, K. R., Kemp, D. J. and Brown, G.V. (1984) *Nature* (London) 310, 789–792; and therefore may be a potential candidate for a vaccine antigen. McGarvey et al. constructed a cDNA library with mRNA from asynchronous cultures of *P. falciparum*. They used differential screening with radiolabeled cDNA from either early or late stage parasites to identify cDNA clones corresponding to 12 genes expressed only during schizogony. They also obtained expression in *Escherichia coli* of some of these schizont-specific genes inserted in the inducible expression vector pPL31A.

There have been other reports of P. falciparum merozoite surface proteins similar in molecular weight to the antigenic proteins described herein. For instance, Jungery, M., Boyle, D., Patel, T., Pasvol, G. and Weatherall, D. J. (1983) *Nature* (London) 301, 704–705 disclosed that erythrocyte glycophorins, thought to serve as receptors for invading merozoites, bound to *P. falciparum* proteins of 140k and 70k which were synthesized during schizogony, and are inferred to be located on the merozoite surface. The results of immunoprecipitation experiments with immune human sera from different parts of the world have defined several *P. falciparum* proteins which may be important in protective immunity; Reese, R. T., Motyl, M. R. and Hofer-Warbinek, R. (1981) *Am. J. Trop. Med. Hyg.* 30, 1168–1178; Perrin, L. H., Dayal, R. and Rieder, H. (1981) *Trans. R. Soc. Trop. Med. Hyg.* 75, 163–165; Brown, G. V., Anders, R. F. and Knowles, G., (1983) *Infect. Immun.* 39, 1228–1235. Monoclonal antibodies to *P. falciparum* antigens have also been used to define possible protective antigens. A 140k protein is among those recognized by monoclonal antibodies inhibiting the in vitro growth of asexual stages; Perrin et al. Inhibitory monoclonal antibodies have also been characterized which bind to an antigen of $M_r$ of greater than 220k; Saul, A., Myler, P., Schofield, L. and Kidson, C. (1984) *Parasite Immunol.* 6, 39–50.

Evidence for the protective role of proteins of approximately 200k, 140k, and 75k has also been obtained from vaccination trials. Dubois, P., Dedet, J. P., Fandeur, T., Roussilhon, C., Jendoubi M., Pauillac, S., Mercereau-Puijalon, O. and Pereira Da Silva, L. (1984) *Proc. Natl. Acad. Sci. U.S.A.* 81, 229–232 disclosed successful vaccination of squirrel monkeys with a schizont protein fraction eluted from the 75k region of a gel, and Perrin, L. H., Merkli, B., Loche, M., Chizzolini, C., Smart, J. and Richle, R. (1984) *J. Exp. Med.* 160, 441–451 reported protective immunization of two groups of squirrel monkeys with partially purified proteins of $M_r$ greater than 200k and 140k respectively, believed to be located on the surface of either schizonts or merozoites.

The present invention comprises DNA sequences which encode proteins or fragments of proteins (polypeptides) present as antigens on the surface of Plasmodium merozoites, in particular *Plasmodium falciparum* merozoites. These proteins include proteins of approximate molecular weights 75,000 (75k protein), 140,000 (140k protein) and 180,000 (180k protein). The invention includes DNA sequences encoding antigenic surface fragments of the 75k protein, 140k protein and 180k protein, as well as DNA sequences encoding the 75k protein, 140k protein and 180k protein (i.e., the genes for these proteins).

The DNA sequences of the invention may be isolated from *Plasmodium falciparum* or synthesized using genetic engineering techniques. DNA or corresponding mRNA can be obtained from late-stage (asexual stage) forms of the *P. falciparum* parasite, e.g., trophozoites (mature), schizonts and merozoites. The invention embraces this DNA and DNA substantially homologous to the DNA, including such DNA in essentially pure form. The invention embraces the DNA sequences produced as cDNA sequences, as well as recombinant plasmids or other recombinant expression vectors (cloning vectors) containing the DNA sequences, and bacterial strains (e.g., *E. coli*) into which such plasmids have been introduced. The DNA sequences, plasmids and bacterial strains are useful in producing the antigenic proteins and protein fragments of the invention. DNA sequences encoding the antigenic protein fragments are also of use as probes for isolating the genes for the corresponding proteins.

The protein fragments and proteins of the invention, which can be prepared from the corresponding DNA sequences, are useful for immunologic and diagnostic purposes. The invention also embraces the preparation of such protein fragments, proteins and DNA. The protein fragments and proteins can function as antigens in giving rise to antibodies to the merozoite form of the parasite and have utility as vaccines, either alone or in conjunction with antigens to the sporozoite and gametocyte forms of Plasmodia (polyvalent vaccine). The protein fragments and proteins also have use in detecting, in vivo or in vitro, the presence of antibodies based on an immunological reaction. In addition, antibodies produced by introduction of the protein fragments and proteins of the invention into a host animal have use, in vivo or in vitro, in assessing for the presence of asexual forms of the parasite.

The DNA sequences of the invention corresponding to antigenic surface protein fragments of the 75k, 140k and 180k proteins have been deposited with the American Type Culture Collection, Rockville, Md. (ATCC) as, respectively, deposit accession numbers 53262, 53261, and 53260. Each deposit is an *E. coli* strain containing a recombinant pUC8 plasmid into which the respective DNA sequence (produced using cDNA techniques as cDNA clones C7, C5 and E4, respectively, as disclosed below) has been introduced. The deposits can be used as a source of DNA to probe for the corresponding genes from which the respective proteins can be produced, and as a source of DNA to produce the corresponding protein fragments.

The invention is based on the construction of a cDNA expression library made from late stage *P. falciparum* mRNA, and the isolation of bacterial clones encoding schizont an merozoite antigens. The library was constructed in the vector pUC8 Vieira, J. and Messing, J. (1982) Gene 19, 259–268; Helfman, D. M., Feramisco, J. R., Fiddes, J. C., Thomas, G. P. and Hughes, S. H. (1983) *Proc. Natl. Acad. Sci. U.S.A.* 80, 31–35, and clones expressing plasmodial antigens were identified by immunological screening with sera from immune Aotus monkeys. Immune Aotus sera inhibit growth of the parasite in culture, Reese, R. T. and Motyl, M. R. (1979) *J. Immunol.* 123, 1894–1899, provide passive immunity to naive animals upon transfer, and are known to contain antibodies which bind to the surface of merozoites and parasitized erythrocytes, Langreth, S. G. and Reese, R. T. (1979) *J. Exp. Med.* 150, 1241–1254. Lysates of bacterial clones identified by the *Aotus* sera were used to immunize mice. The mouse sera were tested for reactivity to plasmodial antigens by immunoprecipitation, by protein electrophoresis and immunoblotting, and by indirect immunofluorescence on both fixed and intact cells. These assays allowed the identification of the blood stage antigens encoded by several cDNA clones. Indirect immunofluorescence on intact extracellular merozoites showed that at least three different antigens appeared to be located on the merozoite surface, making them strong candidates for host-protective antigens. The procedures used in carrying out preparative steps of the invention are more specifically described below.

Parasite culture

The Honduras I isolate of *P. falciparum* (CDC, Atlanta) was cultured using standard methods, Trager, W. and Jensen, J. B. (1976) *Science* 193, 673–675. Cultures were routinely started from cryogenically preserved stocks every three months to minimize any changes which might occur in the parasites during long-term cultivation, Langreth, S. G., Reese, R. T., Motyl, M. R. and Trager, W (1979) *Exp. Parasitol.* 48, 213–219. Mature parasites were separated from ring-stage parasites with Physiogel, Reese, R. T., Langreth, S. G. and Trager, W. (1979) *Bulletin W.H.O.* 57, 53–61, and then stored under liquid nitrogen.

mRNA preparation

Frozen cell pellets were rapidly lysed in 4M guanidinium thiocyanate, 0.1M 2-mercaptoethanol, 25mM sodium citrate and 0.5% N-lauroyl-sarcosine, Chirgwin, J. M., Przybyla, A. E., MacDonald, R. J. and Rutter, W. J. (1979) *Biochemistry* 18, 5294–5298. DNA in the lysate was sheared by several passages through a 25 gauge needle, and the RNA was pelleted through a cushion of 5.7M cesium chloride by centrifugation at 35,000 rpm in a Beckman SW50.1 rotor overnight at 15° C. Poly (A)+ RNA was selected by two cycles of oligodT cellulose chromatography, Aviv, H. and Leder, P. (1972) *Proc. Natl. Acad. Sci. U.S.A.* 69, 1408–1412. To test the integrity of each poly (A)+ RNA preparation, it was translated in a rabbit reticulocyte cell free extract, Pelham, H. R. B. and Jackson, R. J. (1976) *Eur. J. Biochem.* 67, 247–256 and the pattern of total translated products, Gritzmacher, C. A. and Reese, R. T. (1982) *Biosci. Rep.* 2, 667–673; Hyde, J. E., Goman, M., Hall, R., Osland, A., Hope, I. A., Langsley, G., Zolg, J. W. and Scaife, J. G. (1984) Mol. Biochem. Parasitol. 10, 269–285, was examined by $NaDodSO_4$ polyacrylamide gel electrophoresis, Laemmli, U. K. (1970) Nature (London) 227, 680–682.

Construction of cDNA clones in pUC8 pUC8 plasmid DNA was digested with Eco RI and Sal I endonucleases and the 2.7 kilo base pair (kbp) fragment was separated from the 18 bp fragment by agarose gel electrophoresis. The large fragment was recovered by electrophoresis onto a DEAE-membrane, (NA45, Schleicher and Schuell) followed by elution in 1M NaCl, 50mM arginine base at 70° C. for 90 mins, phenol extraction and ethanol precipitation. Beginning with 12.5 ug of poly (A)+ RNA, double stranded cDNA was prepared by standard procedures, Maniatis, T., Fritsch, E. F. and Sambrook, J. (1982) *Molecular Cloning : A Laboratory Manual* (Cold Spring Harbor Laboratory, Cold Spring Harbor, N.Y.). Sal I octanucleotide linkers (New England BioLabs) were first ligated to the cDNA at the ends equivalent to the 3' termini of the mRNA. Following treatment with nuclease S1 and filling-in with the Klenow fragment of polymerase I (New England BioLabs), Eco RI decanucleotide linkers (New England BioLabs) were ligated to the cDNA. The cDNA was then digested with an excess of Eco RI and Sal I and fractionated on a 1.5% agarose gel. Two size classes of cDNA molecules (200 bp to 900 bp, and 900 bp to 4.3 kbp) were purified as described above by electrophoresis onto DEAE membrane filters. About 350 ngs of cDNA were obtained in each size class.

cDNA was ligated to vector at a weight ratio of 1:20, then used to transform the *E. coli* strain DHI by the high efficiency procedure of Hanahan, D. (1983) *J. Mol. Biol.* 166, 57–580. Transformants were plated on LB-ampicillin agar and harvested by scraping the plates, using LB medium to resuspend the bacteria. These suspensions were stored in 7% DMSO, at −80° C. in 15 pools containing from 200 to 3000 independent transformants each.

Immunological Screenino of Bacterial Colonies

Sera from two Aotus monkeys, M33 and M39, were pooled in equal volumes. Monkey 33 (karyotype III) had been immunized as described by Reese, R. T. and Motyl, M. R. (1979) *J. Immunol.* 123, 1894–1899, with *P. falciparum* strains FCR-3, Trager, W. and Jensen, J. B. (1976) *Science* 193, 673–675 and Honduras I; monkey 39 (karyotype VI) was only exposed to FCR-3. Normal serum from monkey 202 (karyotype VI) was used as a control. Sera were preabsorbed with equal volumes of lysates of DH1 containing pUC8. The lysates were prepared by concentrating a stationary culture of DHI 100-fold in 50mM Tris-HCl pH7.6., 150mM NaCl, 0.5% NP40, and boiling the cells for 20 mins. Preabsorption was for 1 hr at 4° C., and was repeated four times. Bacterial colonies were plated on Millipore Triton-free HATF filters and two replicas were made from each master filter. Colonies on the two replicas were lysed by $CHCl_3$ vapor, and subsequently treated as described by Helfman, D. M., Feramisco, J. R., Fiddes, J. C., Thomas, G. P. and Hughes, S. H. (1983) *Proc. Natl. Acad. Sci. U.S.A.* 80, 31–35, except that 1% casein replaced bovine serum albumin in all incubations. The preabsorbed Aotus serum was used at a final dilution of 1/300. The second antibody was affinity-purified rabbit anti-Aotus IgG, labeled with $^{125}I$ to a specific activity of $10^7$ cpm/ug by the chloramine T procedure, McConahey, P. J. and Dixon, F. J. (1966) *Int. Arch. Allergy* 29, 185–189.

Immunization of Mice with Bacterial Lysates

Exponentially growing cultures of cDNA clones were concentrated 10-fold in 0.05% Triton X-100/50 mM Tris-HCl, pH 8.0/12.5 mM EDTA/2 mM phenylmethylsulfonyl fluoride containing lysozyme at 200 ug/ml, leupeptin at 10 ug/ml, and pepstatin at 10 ug/ml. $MgCl_2$ was added to 20mM, and DNase I to 10 ug/ml. Lysates were stored frozen at −70° C. Two mice (C3H or Balb/C strain) were injected i.p. per lysate; each received 200 ul of lysate emulsified with 300 $\mu l$ of Freund's complete adjuvant Mice received two booster shots; on day 21, by s.c. injection of 150 $\mu l$ of lysate emulsified in Freund's incomplete adjuvant, and, on day 36 by i.p. injection of 150 ul of aqueous lysate. Mice were bled 12 days after the first booster shot, and every two weeks thereafter. Antiserum against *E. coli* strain DH1 containing pUC8 was used as the negative control in all experiments with the mouse sera.

Transfer of Proteins to Nitrocellulose and Detection of Antigens

Late-stage *P. falciparum* cultures were concentrated to 70–80% parasitemia with Physiogel, resuspended in 10 volumes of 10mM sodium phosphate pH 7.2 to release soluble erythrocyte proteins, and centrifuged. Proteins in the pellet were solubilized by boiling in sample buffer and resolved by $NaDodSO_4$/polyacrylamide gel electrophoresis on 8% gels, Laemmli, U. K. (1970) *Nature* (London) 227, 680-682 (50 ug total protein per lane), and then electrophoretically transferred to nitrocellulose, Towbin, H., Staehelin, T. and Gordon, J. (1979) *Proc. Natl. Acad. Sci. U.S.A.* 76, 4350–4354.

The nitrocellulose sheets were incubated in 50mM Tris-HCl pH 7.6, 150mM NaCl, with 1% casein for 1–16 hrs., and then probed with individual mouse sera at 1/50 dilution in the same buffer. The nitrocellulose was then washed 3 times in Tris-NaCl with 0.05% Tween 20, treated with $^{125}I$-labeled affinity-purified rabbit anti-mouse IgG (Specific activity $10^7$ cpm/ug), washed 4 times, and autoradiographed as described Howard, R. F. and Reese, R. T. (1984) *Mol. Biochem. Parasitol.* 10, 319–334.

Biosynthetic labelinq and immunoprecipitation

Trophozoites were concentrated by Physiogel treatment and $2 \times 10^8$ infected cells were grown for 12–18 hrs. in 10ml methionine-free RPMI medium (Irvine Scientific) with 15% human serum and 1 mCi of $^{35}S$-methionine (Amersham, 1400 Ci/mmol). Infected erythrocytes and free merozoites were pelleted, resuspended at $10^8$ cpm/ml in 50mM Tris-HCl pH 7.2, 0.5M NaCl, 20mM EDTA, 0.5% Triton X-100, 0.1% SDS, 10 ug/ml leupeptin, 10 ug/ml pepstatin (wash buffer), and centrifuged for 45 min. at 35000 rpm in an SW 50.1 rotor.

Lysates ($2 \times 10^6$ cpm per sample) were preadsorbed at 4° C. for 1 hr. with 0.25 volumes of normal mouse serum, treated for another hr. with 0.5 volumes of packed Protein A-Sepharose beads (Pharmacia), and centrifuged at 15000 g. The supernatants were incubated with 20 ul of immune mouse serum and 40 ul of 50mM Tris-HCl pH7.2, 0.5M NaCl, 20mM EDTA, 0.5% Triton X-100, 1% Casein at 4° C. for 1.5 hr., following which the mixture was absorbed with 25 ul packed, swelled Protein-A Sepharose beads, for another 1.5 hrs. at 4° C. The beads were washed 5 times, using 1 ml of wash buffer each time, resuspended in 2x sample buffer, Laemmli, U. K. (1970) *Nature* (London) 227, 680–682, and boiled for 3 mins. Proteins were resolved on 8% $NaDodSO_4$/polyacrylamide gels, treated with Amplify (Amersham) and fluorographed.

Immunofluorescence on Fixed Cells

Smears were made from a 50% suspension of concentrated late-stage parasites in phosphate-buffered saline (PBS) containing 50% horse serum. Slides carrying the air-dried smears were stored desiccated at −20° C. Immediately before antibody treatment, the smears were fixed for 1 min in acetone at −20° C., then washed four times in distilled water. Smears were incubated for 1 hour at room temperature with drops of 1/10 dilution of the specific mouse serum, washed three times in PBS, treated with drops of a 1/50 dilution of fluorescein-conjugated goat anti-mouse immunoglobulin (Tago), washed three times in PBS, mounted in glycerol, and photographed under UV light through a Zeiss microscope, using Kodacolor 400ASA film or Ektachrome P800/1600 film push-processed to 3200 ASA.

Immunofluorescence on Intact Merozoites

Parasite cultures were synchronized and concentrated at the trophozoite stage with Physiogel, then returned to culture without the addition of fresh erythrocytes until mature schizonts developed. The schizonts were pelleted, resuspended in RPMI medium with 20% human serum, and incubated at 37° C. until merozoites were released (less than 1 hr.). Erythrocytes were then pelleted at 400 g for 10 min., and merozoites were harvested from the supernatant by centrifugation at 1300 g for 10 min. Merozoites were washed once in RPMI, briefly fixed in 0.08% glutaraldehyde (EM grade), washed three times in RPMI and pelleted in microfuge tubes. Such glutaraldehyde treatment stabilizes merozoites but does not permeabilize them or destroy their antigenicity, Stanley, H. A., Langreth, S. G., Reese, R. T., and Trager, W. (1982) *J. Parasitol.* 68, 1059–1067. The lightly fixed merozoites were treated with mouse serum and fluorescein conjugated goat anti-mouse immunoglobulin exactly as described for the fixed-parasite smears, and were examined by fluorescence microscopy.

Thus, in accordance with the above described procedure, RNA from mature trophozoites and schizonts of *P. falciparum* was used to construct a cDNA library in the expression vector pUC8. cDNA inserted between the Eco RI and Sal I sites of pUC8 can be expressed from the transcriptional and translational signals of the lac Z gene which are located upstream of the Eco RI, site Vieira, J. and Messing, J. (1982) *Gene* 19, 259–268. Sequential addition of linkers to the cDNA, as described in Helfman, D. M., Feramisco, J. R., Fiddes, J. C., Thomas, G. P. and Hughes, S. H. (1983) *Proc. Natl. Acad. Sci. U.S.A.* 80, 31–35, was used to ensure that a high percentage of cDNA molecules would be inserted in the correct orientation for expression. The yield of clones from the two size classes of fractionated cDNA was markedly different. Only 6,000clones were obtained from 270 ng of the larger size class (900 bp to 4,300 bp, class A) whereas the small size class (200 bp to 900 bp, class B) yielded 26,000 clones from 180 ng cDNA.

Plasmid DNA was prepared from a few cDNA clones of both size classes, and the insert sizes were examined by agarose gel electrophoresis following digestion of the DNA with Eco RI and Sal I. 70% of the clones in class B and 50% of those in class A contained inserts of the expected sizes; the rest apparently contained no cDNA, and probably resulted from head to tail ligation of vector molecules. The cDNA inserts from a few clones were purified and used as hybridization probes on blots, Southern, E. M. (1975) *J. Mol. Biol.* 98, 503–517, of restriction digests of *P. falciparum* DNA in order to confirm that the cloned fragments did indeed correspond to plasmodial sequences.

When the clones were screened with immune Aotus sera for expression of plasmodial antigens, about 2.5% of the clones from class B were positive, while only 0.5% of the class A clones reacted. A total of 8,000 colonies from class B and 1000 from class A were screened. Clones reacting with Aotus serum were picked, replated on filters at a density of about 100 colonies per plate of 10 cm diameter and rescreened in duplicate to confirm their antigenicity, and also for single colony purification. 95 positive clones were accumulated, 91 from class B and 4 from class A. These clones may not all have been independent since the library was amplified after the initial transformation.

Most of the cDNA clones which reacted positively with the Aotus sera contained small inserts (250–900 bp) and so were unlikely to be expressing full-length parasite proteins. In order to identify the plasmodial proteins corresponding to the antigens expressed from the cloned cDNA fragments, mice were immunized with extracts of several clones, and then three different immunological techniques were used to screen these mouse sera for reactivity with parasite antigens. Before they were injected into mice, the bacterial lysates were spotted on nitrocellulose and tested for reactivity with monkey sera. About one-third of the clones lost their antigenicity during the preparation of the lysates, perhaps due to the degradation of the expressed peptide, and these were not used as immunogens.

Mouse sera were obtained against forty-nine bacterial clones. Of these sera, 24 were able to precipitate labeled plasmodial proteins in an immunoprecipitation assay, and 21 of the same 24, as well as 9 others, a total of thirty, detected specific antigens on nitrocellulose blots of electrophoretically resolved proteins from parasitized cells. In addition, 32 of the 49 sera reacted with antigens of parasitized erythrocytes when tested by indirect immunofluorescence on slides of fixed parasites. Three of the parasite antigens identified by these methods appear to be located on the merozoite surface and are described here in more detail.

Mouse sera raised against the three cDNA clones B10 (pfB-10), C1 (pfC-1) and C7 (pfC-7), all gave a similar pattern of strong surface fluorescence with intact extracellular merozoites. The antigen recognized by these sera was also present in trophozoites and schizonts, as determined by immunofluorescence on fixed parasitized cells. All three sera precipitated a *P. falciparum* protein of $M_r$ 75K, as well as a minor protein species at 225k. Western blotting experiments with any of these three sera resulted in the same protein pattern as produced by immunoprecipitation, although the 225k protein was not always detected.

C5 (pfC-5) was another cDNA clone which appeared to encode a merozoite surface antigen, as determined by immunofluorescence on intact parasites. The fluorescence pattern was essentially the same as that of C7, albeit somewhat weaker. Mouse antiserum to C5 immunoprecipitated a protein of $M_r$ 140k. However, in Western blots of proteins of parasitized erythrocytes, anti-C5 serum reacted with three proteins having approximate molecular weights of 140k, 68k and 45k. The relative proportions of these three protein species varied in different antigen preparations.

A protein with an approximate molecular weight of 180k was precipitated from extracts of 35S-labeled parasite proteins by mouse serum raised against clone E4

(pfE-4). In addition, in some experiments, anti-E4 serum precipitated a protein of $M_r$ 59k. Anti-E4 serum did not react convincingly with any parasite protein in immunoblotting experiments, suggesting that the epitopes recognized by this serum were destroyed by boiling in 2% NaDodSO4 under reducing conditions. The antigen corresponding to clone E4 also shared the fluorescence pattern of the C7 antigen, and thus appeared to be localized to the merozoite surface. The high molecular weight plasmodial protein corresponding to the clone E4 did not co-migrate on NaDodSO4-polyacrylamide gels with gp185, the schizont glycoprotein which has been extensively described in the literature and which is believed to be a precursor to some of the major merozoite proteins, Freeman, R. R. and Holder, A. A. (1983) J. Exp. Med. 158, 1647–1653.

The results of the colony immunoassay of the P. falciparum cDNA library, permit estimate that the library should contain approximately 600–700 clones expressing antigens recognized by immune Aotus sera, although each positive clone Will not be the product of an independent cloning event since the library Was amplified. McGarvey et al. have suggested that only twelve major gene families are expressed specifically in the schizont and merozoite stages. Since it appears that antigens expressed in schizonts and merozoites play a major part in eliciting protective immunity against malaria this collection of several hundred clones expressing late-stage P. falciparum antigens should include clones for many of the important protective antigens for the asexual cycle.

It is not clear why the fraction of clones reacting with Aotus serum was lower in the clone pools with larger cDNA inserts (class A). One -possible explanation is that large foreign polypeptides expressed constitutively in E. coli may be more susceptible to degradation than smaller ones, making the parasite antigens expressed in class A clones relatively unstable, and thus difficult to detect.

Mice were selectively immunized with lysates which were antigenically positive with serum from monkeys immune to P. falciparum. Consequently, most (32/49) of the mouse sera obtained reacted with parasite antigens. However, the positive anti-parasite responses were only detected 2 to 3 months after immunization of the mice, and were weak in many cases, perhaps due to low concentrations of the expressed plasmodial protein in the bacterial lysates.

Polyclonal, mono-specific sera against particular plasmodial -proteins are scarce because of technical difficulties encountered in purifying individual parasite proteins. Therefore, the mouse sera obtained by the methods of this invention are valuable reagents, as each one is specific for the single plasmodial protein encoded by the cDNA clone used for immunization.

Each of the cDNA clones used to raise antibodies against these three different antigens was genetically purified and contained only one cDNA fragment. Yet each of the three antisera against clones C7, C5 and E4 recognized more than one protein species, either in immunoblotting or immunoprecipitation experiments. These proteins have been ascribed molecular weights of 75k, 225k (C7), 140k, 68k, 45k (C5) and 180k, 59k (E4). It remains to be elucidated whether the multiple protein bands observed for each cloned antigen are immunologically cross-reactive products of different genes, whether there is a precursor-product relationship between the protein species, or whether the multiple bands are an artifactual result of proteolysis during sample preparation. The results show that epitopes related to those encoded by each of the cloned gene fragments are located on the merozoite surface.

For malarial antigens to play a protective role in immunity, they should be exposed to the immune system on the surface of either the infected erythrocyte or the merozoite. The results of indirect immunofluorescence assays indicated that the three specific antigens of the invention all appeared to be located on the merozoite surface. These molecules have utility in the development of a general P. falciparum vaccine, especially as the evidence to date indicates they are not strain-specific for the Honduras I isolate.

What is claimed is:

1. An isolated and purified DNA molecule selected from the group consisting of a P. falciparum Honduras I DNA sequence located between the Eco RI and Sal I endonucleus sites within recombinant plasmid pfC-7 which DNA sequence encodes a merozoite surface antigen having a molecular weight of approximately 75,000 or an antigenic portion thereof, and a nucleotide sequence that hybridizes to said DNA sequence and which encodes a P. falciparum antigen having a molecular weight of approximately 75,000.

2. An isolated and purified DNA molecule selected from the group consisting of a P. falciparum Honduras I DNA sequence located between the Eco RI and Sal I endonuclease sites within recombinant plasmid pfC-5 which DNA sequence encodes a merozoite surface antigen having a molecular weight of approximately 140,000 or an antigenic portion thereof, and a nucleotide sequence that hybridizes to said DNA sequence and which encodes a P. falciparum antigen having a molecular weight of approximately 140,000.

3. A recombinant expression vector which comprises the DNA sequence of claim 1.

4. A recombinant expression vector which comprises the DNA sequence of claim 2.

5. A host cell transformed with a recombinant expression vector according to claim 3.

6. A host cell transformed with a recombinant expression vector according to claim 4.

* * * * *